(12) United States Patent
Landy

(10) Patent No.: US 11,701,035 B2
(45) Date of Patent: Jul. 18, 2023

(54) NONINVASIVE BLOOD GLUCOSE DETECTOR AND METHOD USING IR

(71) Applicant: Bruce M. Landy, Parker, CO (US)

(72) Inventor: Bruce M. Landy, Parker, CO (US)

( * ) Notice: Subject to any disclaimer, the term of this patent is extended or adjusted under 35 U.S.C. 154(b) by 855 days.

(21) Appl. No.: 16/665,536

(22) Filed: Oct. 28, 2019

(65) Prior Publication Data

US 2021/0121104 A1    Apr. 29, 2021

(51) Int. Cl.
    *A61B 5/145*     (2006.01)
    *A61B 5/1455*    (2006.01)
    *A61B 5/00*      (2006.01)

(52) U.S. Cl.
    CPC ........ *A61B 5/14532* (2013.01); *A61B 5/1455* (2013.01); *A61B 5/6815* (2013.01); *A61B 5/6825* (2013.01); *A61B 5/6844* (2013.01); *A61B 5/742* (2013.01); *A61B 5/7405* (2013.01); *A61B 5/7475* (2013.01); *A61B 2560/0406* (2013.01)

(58) Field of Classification Search
    CPC . A61B 5/14532; A61B 5/1455; A61B 5/6815; A61B 5/6825; A61B 5/6844; A61B 5/7405; A61B 5/742; A61B 5/7475; A61B 2560/0406
    See application file for complete search history.

(56) References Cited

U.S. PATENT DOCUMENTS

| | | | |
|---|---|---|---|
| 4,281,645 A | 8/1981 | Jobsis | |
| 5,370,114 A | 12/1994 | Wong et al. | |
| 5,379,764 A | 1/1995 | Barnes et al. | |
| 5,529,755 A | 6/1996 | Higashio et al. | |
| 5,553,613 A | 9/1996 | Parker | |
| 5,601,080 A | 2/1997 | Oppenheimer | |
| 5,692,504 A | 12/1997 | Essenpreis et al. | |
| 5,743,262 A | 4/1998 | Lepper, Jr. et al. | |
| 5,782,756 A | 7/1998 | Mannheimer | |
| 5,818,048 A | 10/1998 | Sodickson et al. | |
| 5,803,132 A | 11/1998 | Robinson | |
| 5,840,023 A | 11/1998 | Oraevsky et al. | |
| 6,165,440 A | 12/2000 | Esenaliev | |
| 6,309,352 B1 | 10/2001 | Oraevsky et al. | |
| 6,466,807 B1 | 10/2002 | Dobson et al. | |
| 6,498,942 B1 | 12/2002 | Esenaliev et al. | |
| 6,725,073 B1 | 4/2004 | Motamedi et al. | |
| 6,751,490 B2 | 6/2004 | Esenaliev et al. | |
| 7,430,445 B2 | 9/2008 | Esenaliev et al. | |

(Continued)

*Primary Examiner* — Eric F Winakur

(74) *Attorney, Agent, or Firm* — Robert C. Kain; Scott D. Smiley; The Concept Law Group, P.A.

(57) ABSTRACT

The blood glucose (BG) detector (BGD) stores baseline BG data therein. The BGD has a housing with legs forming a U-shaped sensing channel for a finger web or ear antihelix. The sensory channel limits insertion of the web/antihelix. A positional light sensor subsystem audibly and/or visually indicates a test-to-test detection position. A BG sensor on the legs uses IR 1550 bandwidth light to detect BG by transmission through the web/antihelix ro generate a detected BG signal. A comparator (in processor-memory system) compares detected BG signal to baseline BG data and generates a displayable BG level to the user via a display module. Alternatively, a leg-to-leg distance sensor may be used. A keypad enables upload of the BD baseline data (or an I/O port).

22 Claims, 5 Drawing Sheets

(56) References Cited

U.S. PATENT DOCUMENTS

| | | | |
|---|---|---|---|
| 8,135,450 B2 | 3/2012 | Esenaliev et al. | |
| 8,306,593 B2* | 11/2012 | Hwang | A61B 5/6838 |
| | | | 600/335 |
| 8,346,328 B2* | 1/2013 | Mannheimer | A61B 5/6843 |
| | | | 600/310 |
| 2004/0127777 A1 | 7/2004 | Ruchti et al. | |
| 2004/0220459 A1* | 11/2004 | Schlegel | A61B 5/14532 |
| | | | 600/316 |
| 2005/0272990 A1* | 12/2005 | Ariav | A61B 5/14532 |
| | | | 600/365 |
| 2007/0255141 A1 | 11/2007 | Esenaliev et al. | |
| 2009/0062632 A1* | 3/2009 | Rebec | A61B 5/1455 |
| | | | 600/316 |

* cited by examiner

NONINVASIVE BLOOD GLUCOSE DETECTOR AND METHOD USING IR

The present invention relates to a blood glucose detection system and a method using infrared (IR) light in a 1550 nm bandwidth range wherein the 1550 nm bandwidth range is 1085 nm to 2015 nm.

BACKGROUND OF THE INVENTION

Prior art references show the use of 1550 nm light to detect blood glucose (BG). A typical IR range is 700 nanometers (nm) to 1 millimeter (mm)). U.S. Pat. No. 5,370,114 to Wong discloses a finger blood glucose detector using a non-invasive blood chemistry measurement by stimulated infrared relaxation emission. The Wong apparatus measures the concentration of blood components, such as blood glucose. A beam of exposing light is imaged through a wall of a containment vessel onto a region of the sample adjacent to this wall. Wong '144 also discloses that, in the fingerprint region, only glucose and haemoglobin exhibit intense absorption at certain wavelengths. Wong states "Only the following five wave numbers give enough sensitivity for measurement of blood glucose: 1040, 1085, 1109, 1160 and 1365 cm-1. Only the 1040 cm-1 band is free of superimposed absorption of other blood constituents, and only glucose and haemoglobin exhibit intense absorption at 1109 cm-1. Therefore, the most attractive choices for monitoring blood glucose levels are the 1040 and 1109 cm-1 absorption bands."

Further, Wong states "The 0.6-1.5 microns (16,667 cm-1 [600 nm]-6,667 cm-1 [1550 nm]) range is selected for the exposing light because it can pass, without significant attenuation, through the epidermis [ ]. Preferably, the exposing light is within the range from 0.6-1.1 microns, because this range not only passes through the epidermis without undue attenuation, as illustrated . . . , it is also effective in exciting haemoglobin molecules, so that pressure-related changes in the amount of blood in papillary bed [ ] can be compensated for from a knowledge of the amount of absorption by the haemoglobin molecules."

The prior art also discloses an anti-helix blood glucose detector (BGD). U.S. Pat. No. 10,015,582 to Wagner discloses a device that reflects light off the user's skin. The Wagner device can engage a particular portion of the body of a user. For example, in some embodiments, the BG sensor module may be incorporated into an earbud and the housing outer surface is contoured to matingly engage a particular region of the ear (e.g., the region between the anti-tragus and the concha, the region along the helix or anti-helix of the ear). Wagner's light guides may lead to any region of the ear, such as the ear canal, tympanic membrane, earlobe, helix, antihelix, tragus, behind the ear, temple, etc.

U.S. Pat. No. 5,379,764 to Barnes discloses a non-invasive determination of analyte concentration in body of mammals. According to Barnes, the intensity of the reflected radiation as a function of wavelength in the near infrared band of glucose between 1100 nm and 1900 nm, yielded effective data from which glucose concentrations can be derived. Barnes shows that the IR light is transmitted into the skin and then reflected back from the internal organ in the body. The Barnes fiber-optic probe includes an input radiation conductor for transmitting radiation to a portion of an ear lobe or wrist, of the patient's body and a pickup or sensing radiation conductor for receiving the resulting radiation from the body portion.

Barnes discusses placing the IR transmitter on one side of a body part and the IR receiver on the other side of the body part. The ends of conductors, instead of being side-by-side in contact with adjacent surfaces of the body portion, are in contact with the outer surfaces on opposite sides of the body portion, for example, with opposite surfaces of the ear lobe.

Barnes also discusses transmitting the IR beam through either the ear or the finger web. The near infrared radiation from the source can be passed through the portion of the body, which may be the ear lobe, tongue or webbing between the fingers or toes, and its spectral absorption characteristics measured. This is accomplished by placing the body section between the ends of the dual conductor so that the radiation passes through the body section.

However, Barnes does not appreciate that the distance between the transmitter and the receiver is important, only the adjacent nature of the transmitter and the receiver to the skin.

EP Publication 623308 to Wiggins (Wiggins '308) discusses a method for non-invasive measurement of concentration of constituents in blood. Wiggins discloses a transmitter on one side of the earlobe and a receiver on the other side. Infrared or near-infrared radiation, either at selected wavelengths or over a portion of the spectrum is used. Radiation that is either back-scattered or transmitted through a body part such as the finger, is measured.

Wiggins '308 does not address the need for precise positioning of the BGD's U-shaped channel nor the cross-leg IR transmission distance.

The prior art does discuss potential errors caused by poorly positioned BG sensors. U.S. Pat. No. 10,015,582 to Wagner recognizes that positioning the BGD on the skin of the user is important. There may be unwanted optical scatter associated with light bouncing off (i.e., reflecting off) the skin and other body tissues in a manner that is not biometrically modulated (i.e., light that is not interacting with blood flow changes).

U.S. Pat. No. 5,601,080 to Oppenheimer (Oppenheimer '080), states that "In [ ] non-invasive devices, changes in volume and/or emitter-to-detector distance should be minimized. Similarly, in the earlier-described devices, a constant light path between a light source and each detector is beneficial. With respect to the non-invasive devices, a tight fit should be ensured. Rotational movement may be prevented by the use of rubberized, high friction surfaces. Changes in volume and device movement may be minimized by tightening with Velcro® straps."

However, Oppenheimer deals with blood flowing through a tube and not a user's body part.

U.S. Pat. No. 5,830,132 to Robinson discusses issues associated with the distance between the transmitter and the receiver. Robinson discusses a BGD sensing the condition of blood through a finger. Robinson states: "The separation distance is not the sole influence on mean optical pathlength as differences in tissue composition and other physiological parameters will influence the light propagation. With reference to [ ], the source and detector are on the same side of the tissue during partial transmission sampling. Due to their location on the same side of the tissue, tissue thickness has a reduced influence on the measurement. The mean optical pathlength then becomes a function of the separation between source and detector. As previously stated partial transmission sampling will reduce the spectral variation introduce by differences in tissue thickness."

The present invention, with its position sensory feedback, seeks to overcome these prior art problems.

OBJECTS OF THE INVENTION

It is an object of the present invention to provide a blood glucose detector (BGD) which solves the problem of repetitive consistent positioning of the BGD on a user's finger web or anti-helix.

It is another object of the present invention to provide audio feedback and/or visual feedback to the user when the BGD is properly positioned on the finger web or antihelix.

It is a further object of the present invention to provide a compact, easy to program and easy to use BGD.

It is an additional object of the present invention to have a BGD which monitors and alerts the user as to the proper IR transmitter to receiver distance.

SUMMARY OF THE INVENTION

The blood glucose detector (BGD) is adapted to be placed on a user's finger web or an ear's antihelix. The BGD is used in conjunction with earlier, conventionally obtained baseline blood glucose data. The BGD includes a housing having opposing legs extending therefrom. The legs form a substantially U-shaped sensing channel. This channel receives the finger web or ear antihelix during a detection mode. The inboard side of the U-shaped channel, closer to the housing, forms a mechanical stop which limits further insertion of the finger web or ear antihelix during the detection mode.

The BGD includes a positional light sensor substantially adjacent the stop coupled to an audible or lighted indicator system adapted to indicate a detection position to the user. A blood glucose sensor is disposed on one or both of the opposing legs at an outboard position relative to the positional light sensor. The blood glucose sensor transmits light into the finger web or ear antihelix within a 1550 nm bandwidth range. The "1550 nm bandwidth range" is 1085 nm to 2015 nm. The blood glucose sensor generates, with complementary electronic components, a detected blood glucose signal.

A comparator, either as a programmable circuit or configured as a processor with a memory, is coupled to the blood glucose sensor. The comparator compares the then currently detected blood glucose signal with the baseline blood glucose data and generates a displayable blood glucose level during the detection mode. A display module displays the displayable blood glucose level during the detection mode based upon the operations of the comparator and associated circuitry.

Further enhancements include a detection completion indicator system coupled to the comparator to indicate a completed detection cycle to the user substantially upon generation of the displayable blood glucose level. The comparator, in some embodiments, includes a processor and a memory. The processor logs and stores, into memory, the baseline blood glucose data, the detected blood glucose signal and the displayable blood glucose level as logged data (date and time stamped). A data output port may be provided, coupled to the processor and the memory, to output the logged data.

Regarding the opposing legs which extend outboard from the housing, at least one leg may be semi-rigid and flexible such that during the detection mode, such leg is adapted to flex towards the other leg by the user. Different constructions of such semi-rigid but flexible leg include a stress relief joint, a stress relief channel, a hinge coupling the leg to the housing, and a biased pivot joint at the junction of the leg and the housing. The positional light sensor may be spaced away from, but substantially adjacent to, the stop such that the user may compress the flexible leg (or compress both flexible legs together), causing the positional light sensor to activate at the correct leg-to-leg spacing distance. Otherwise, one or the other or both of the legs may include an inwardly protruding detent extending into the U-shaped channel. The detent has a distal surface region spaced apart from the opposing respective leg and also has an outboard detent surface. The positional light sensor (or distance sensor) is optimally located on the distal surface region. The outboard detent surface acts as the stop for the web or ear helix.

In another configuration for the detent carrying positional system, the BGD uses a positional sensor on the distal surface region coupled to the audible or lighted indicator system adapted to indicate a detection position to the user. This positional sensor may omit the positional LED light transmission system and use an induction or magnetic spatial detection sub-system disposed on the legs may be used. Using a Hall element with analog output makes it possible to detect the position of an object by resolving power in the order of a few micrometers for a stroke of 1 mm.

In another embodiment, the BGD uses computer processing chips. The housing can include a processor, a memory, a user's visual display, an input keypad, and an audio annunciation module (a speaker or a integrated circuit having a audio announcing function). In the processor system, the positional light sensor generates positional signals to the processor, and the processor activates audible and lighted indicator sub-systems, via the audio module and the display, to indicate a detection position for the U-shaped channel over the finger web or the antihelix. The blood glucose sensor generates a detected blood glucose signal which is sent to the processor. The processor has a comparator means or program for comparing the detected blood glucose signal with the baseline blood glucose data (this data earlier stored in the memory). Upon a comparison of the detected blood glucose signal with the baseline blood glucose data, the processor generates a signal representing the current BG level which is recognized by the user. The displayable blood glucose level data is applied to the display and read by the user. Further, the processor has a detection completion indicator module which indicates, audibly and/or visually, a completed detection cycle to the user substantially upon generation of the displayable blood glucose level data. The processor logs and stores into the memory the baseline blood glucose data, detected blood glucose signal, and displayable blood glucose level data, all as logged data (that is data with a day and time stamp). An input port is coupled to the processor. The processor's initialization module or program accepts the baseline blood glucose data via the input port and stores the same in the memory. Otherwise, during an initialization phase, the user inputs the BG baseline into the BGD via a keypad. In an enhancement, an input/output port is provided, coupled to the processor. In the processor initialization module, the processor either (a) accepts the baseline blood glucose data via the input/output port and stores the same in the memory, or (b) accepts the baseline blood glucose data input by the user via the keypad. The baseline is stored in memory or captured as programmable data on the comparator IC.

The method for detecting blood glucose via infared (IR) light includes obtaining baseline blood glucose data; storing the baseline blood glucose data in a memory; and providing a substantially U-shaped sensing channel adapted to receive the finger web or ear antihelix during a detection mode. When the web or antihelix is in the U-shaped channel, insertion of the finger web or ear antihelix is limited by the U-shaped sensing channel during the detection mode. Audible and/or visual indicators show the user that a sensing position has been reached when the finger web or ear antihelix is at or adjacent the BGD's mechanical stop. In the sensing position, IR light within the 1550 nm bandwidth is transmitted into the finger web or ear antihelix. A detected blood glucose signal is generated by the method. This detected blood glucose signal is compared against the baseline blood glucose data earlier stored in the memory. Then a blood glucose value is displayed to the user based upon a comparison of the detected blood glucose signal and the baseline blood glucose data. Further, the method indicates, either audibly or visually, a detection completion when the blood glucose value is displayed.

Enhancements to the method include logging and storing into the memory: the baseline blood glucose data, the detected blood glucose signal, and the blood glucose value as logged data. Also, the baseline blood glucose data may be obtained via an input port and this data is then stored in the memory. Further, the baseline blood glucose data may be obtained via a keypad.

As a further summary, the Blood Glucose Detector ("BGD") has the following features or characteristics to detect a user's blood glucose ("BG"). The BGD uses IR light at a 1550 nm wavelength to detect blood glucose. More generally, a 1550 nm "bandwidth range" is used wherein the 1550 nm "bandwidth range" is IR light in the range of 1085 nm to 2015 nm.

In an initialization or set-up phase, the user identifies his/her blood glucose (BG) through a customary detection system(s). This is baseline blood glucose data herein. Thereafter, the user slips or attaches the BGD to his/her finger or his/her ear (on the antihelix portion of the ear) and the BGD senses the user's blood sugar with the IR light differential transmission. The BGD then correlates the previously input blood glucose baseline data or level with the then captured IR transmission data.

In one initialization embodiment, the BGD has a user input element (a small numbered keypad) permitting the user to input the blood glucose baseline data from the conventional BG detector into the BGD. The BG baseline data is matched to the then captured IR light transmission level obtained by the BGD. More precisely, the then captured IR light data is re-labeled as the device's BG baseline data. This captured data is then the baseline BG level for the BGD and the baseline IR transmission signal level. As is known, the lower the sensed IR transmission level from the conventionally established baseline BG level, the higher the then detected user's BG level.

The BGD has a user display which shows the currently detected BG level based upon the then detected BG signal (the captured IR transmission data), as the IR transmision data is correlated to the IR BG baseline.

It is important that for each BG sensing event, the BGD is positioned at the identical or nearly identical physical location on the finger web or antihelix. Hence, embodiments of the invention have certain audible and/or visual feedback systems to alert the user of the proper placement of the BGD on the finger web or antihelix.

In one embodiment, for the finger web, the BGD has a vertical stop which is perpendicular to the finger web, assuring that the IR transmitter and IR receiver is at the same or nearly the same physical location on the web as the initial set-up position when the baseline IR transmit data is collected. The vertical stop is set back from forward pointed or outboard extending legs of the BGD. The vertical stop and forward outboard extending legs form a horizontal U-shaped channel. The user inserts the BGD horizontal U-shaped channel over and on the finger web until the vertical stop of the horizontal U-shaped channel lies against the foremost skin of the finger web. For the finger web, the BGD U-shaped channel is always placed on the same finger web as the user initially captured the IR transmission data for the IR transmit baseline.

On the finger web BGD, the horizontal U-shaped channel may have at least one (maybe two) semi-flexible legs (these legs forming the upper and lower legs of the horizontal U-shaped channel). When the horizontal U-shaped channel (herein the "HU" channel) is fully inserted into and over the finger web, as limited by the foremost edge of the finger web acting on the vertical stop of the HU channel, the user gently press down on one or both of the flexible legs. In this manner, the distance between the IR transmitter on one leg and the IR receiver on the opposing leg is substantially the same over several BGD sensing cycles.

When properly placed, the BGD issues an audible sound and/or light indication alerting the user of the proper placement of the BGD on the finger web. The audio and visual alert indicates to the user that (a) the BDG is at the proper insertion position on the web and (b) the legs are properly spaced apart (the transverse direction) for the BG data capture via the IR transmission system.

To assure leg space-apart distance in the transverse direction, the BGD may use a different wavelength light indicator sub-system to test for cross-leg distance, then issue the audible "proper placement" alarm, also indicating that the IR sensory data was captured for the BG test.

As another alternative, the HU channel may have an LED transmitter and a complementary LED receiver on opposing sides of the HU channel (that is, a transmitter on one leg and an opposing receiver on the other leg). Electronics detects the proper positioning of the BGD legs when the LED position indicator signal drops below a threshold; the threshold being established during the initialization of the BGD. An audible and/or light signal is generated as the position OK signal.

For the antihelix BGD, a similar mechanical system, with a vertically aligned the U-shaped channel and audible position detection is used. Alternatively, a horizontally deployed antihelix BGD system and process is used. Although the discussion herein refers to a "horizontal antihelix" ("HAH") process and a "vertical antihelix" ("VAH") process, a skilled user could train him or herself to place the BGD at any defined angle over the ear and onto the antihelix because, as described below, certain integrated circuits can be set to detect various angular positions. For purposes of discussion of the invention, HAH and VAH are discussed because it is more likely that a user can train him or herself to vertically place the BGD on the antihelix over many sensing cycles rather than angularly locate the BGD over many sensing cycles. The same is true for VAH sensing cycles.

To assure that the angle of attack of the BGD for a VAH process, see FIG. 2, arrow V1, of the U-channel is identical or nearly identical, a "vertical" sensor circuit is used in the BGD to align the U-shaped channel vertically on the ear, over the helix and onto the antihelix. A recent breakthrough in Hall-effect sensing has enabled the creation of omnidirectional magnetic sensor ICs. Advances in IC design and fabrication now support the construction of vertical Hall sensors. The vertical and planar sensors are based on the same physical phenomena but different construction methods: (1) Planar: Laid out across the width and length of the chip; will only sense Z dimension regardless of orientation (2) Vertical: Constructed from top to bottom along the depth of the chip; can be oriented to sense X, Y, or other directions. See https://www.allegromicro.com/en/Insights-and-Innovations/Technical-Documents/Hall-Effect-Sensor-IC-Publications/Vertical-Hall-Tamper-Detection.

With the antihelix BGD version in the VAH process, the U-shaped channel legs are vertically positioned and the channel stop is horizontal, enabling the user to limit the insertion of the HU channel into and over the ear. In one embodiment, the user closes the flexible, depressible legs, when the light transmitters/receivers identify the proper cross-leg distance, and the BGD audibly announces the correct position and the BGD captures the IR transmission data.

If further testing indicates that positional LED light transmissions do not accurately detect the cross-leg distance in either the finger web BGD or the antihelix BGD, then an induction or magnetic spatial detection sub-system disposed on the legs may be used. Using a Hall element with analog output makes it possible to detect the position of an object by resolving power in the order of a few micrometers for a stroke of 1 mm. See https://www.akm.com/akm/en/product/add/magnetic_sensors/0002/.

Once the cross-leg detection sub-system indicates the correct leg spacing distance, the BG is sensed by activating the IR transmitter/receiver set to capture the IR transmission data.

BRIEF DESCRIPTION OF THE DRAWINGS

Further objects and advantages of the present invention can be found in the written description when taken in conjunction with the following drawings.

DETAILED DESCRIPTION OF EMBODIMENTS OF THE INVENTION

The present invention relates to a blood glucose detection (BGD) system and a method using infrared IR light in a 1550 nm bandwidth range. As used herein, the 1550 nm bandwidth range is a range from 1085 nm to 2015 nm. Sometimes this 1550 nm bandwidth range is referred to as the IR BG bandwidth.

Figure 1:
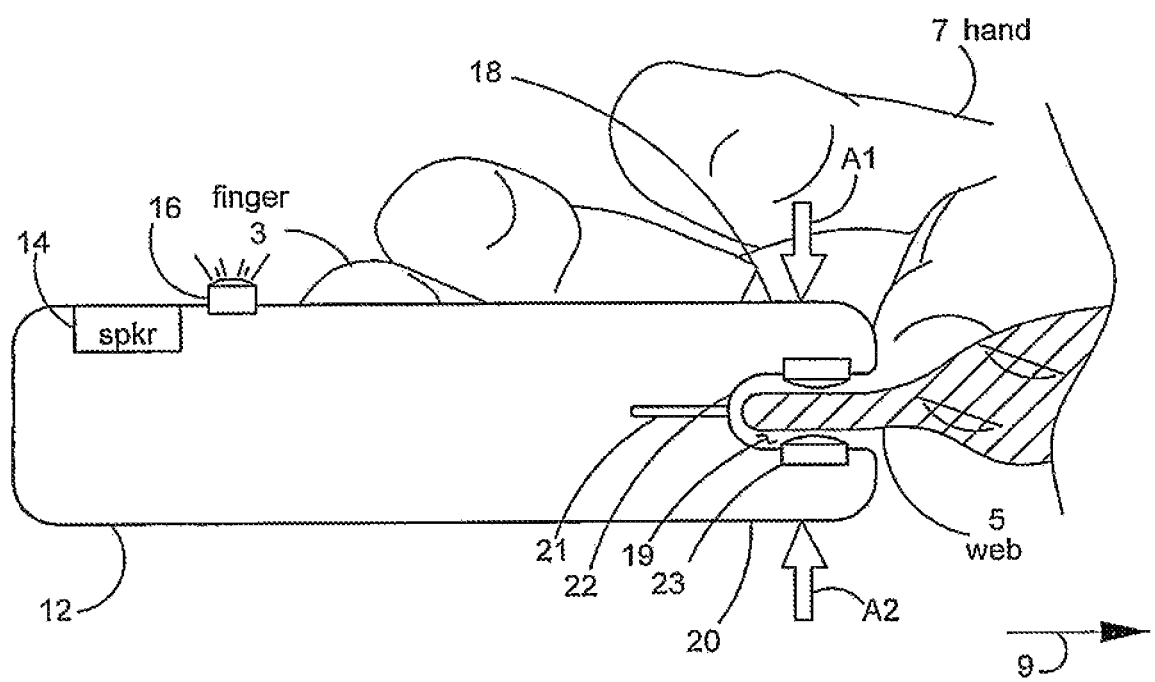
FIG. 1 diagrammatically illustrates the blood glucose detector (BGD) just prior to insertion of the BGD on the user's finger web.
Figure 2:
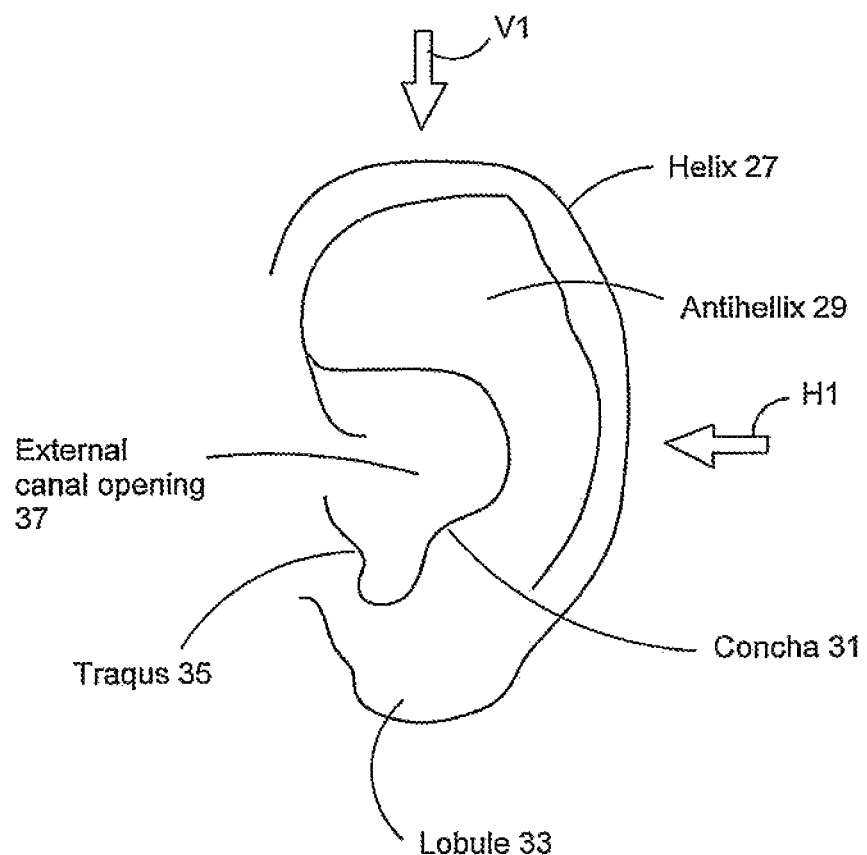
FIG. 2 diagrammatically illustrates the BGD operable on a user's antihelix at different positioning locations (one vertical (V1) and the other horizontal (H1)) for insertion of the BGD over the helix and onto the antihelix. It should be noted that the blood glucose detector (BGD) may be positioned at any angular position on the anti-helix of the user, for example any angle of attack V1 to H1.

FIG. 1 diagrammatically illustrates a BGD in the process of being inserted onto a user's finger web. FIG. 2 diagrammatically illustrates a user's ear and, more importantly, a vertical position arrow V1 and a horizontal position arrow H1 graphically representing potential insertion directions and locations for the BGD to obtain data on blood glucose in conjunction with the user's antihelix. It should be noted in connection with FIG. 2, that the user may capture the antihelix at a variety of different angular locations other than V1 and H1. The important operational aspect for the use of the BGD on the antihelix is the consistent repetitive insertion of the BGD on the antihelix and into the IR transmission channel such that substantially the same location of the antihelix is tested for blood glucose over a number of blood glucose testing cycles. FIGS. 1 and 2 are discussed concurrently herewith. Stated otherwise, the embodiment of the BGD in FIG. 1 can be used on the antihelix in FIG. 2.

Blood glucose detector 12 includes opposing, outboard extending legs 18, 20 at one end of BGD housing 12. The term "outboard" refers to items farther away from the BGD housing 12 (and the term inboard being the opposite). Outboard extending legs 18, 20 form a sensing channel 19 (a substantially U-shaped channel) between the inboard surfaces of the respective legs 18, 20. An IR transmitter 22 is also positioned on the inboard surface of one of the opposing legs 18 and an IR receiver 23 is disposed on the inboard surface of opposing leg 20. In another embodiment, the IR system 22, 23 maybe on a single leg and be angled and configured to reflect light off the blood flow in the finger web or antihelix.

In operation, the user moves BGD 12 such that finger web 5 hand 7 is inserted into sensing channel 19. Finger web 5 is intermediate finger 3 and the adjacent finger which is not illustrated in FIG. 1. When the finger web 5 is disposed in a predetermined position in sensing channel 19, the user is notified, in a preferred embodiment, by an audio announcement generated by speaker 14 and a visual indicator by light 16. See FIG. 3 for a discussion of the positional light sensor subsystem. As discussed later in conjunction with FIG. 3, display panel 44 may be used as the positional visual indicator rather than positional feedback indicator light 16. Also, in order to obtain the correct leg-to-leg channel spacing 19 between opposing legs 18, 20, the user may be required to depress one or both of the legs 18, 20 towards the other opposing leg (force leg 18 in the direction of arrow A1 towards a rigid leg 20; move legs 18,20 in the direction of arrows A1 and A2 causing both legs to move towards each other; or moving leg 20 in direction A2 towards a rigid leg 18). The goal is to teach the user to obtain a repetitively consistent leg-to-leg distance 19 between IR transmitter 22 and IR receiver 23 over each glucose testing cycle. In this manner and in this FIG. 1 embodiment, the BGD has a stress relief channel 21 therein permitting the legs 18, 20 to be somewhat flexed or moved towards and away from each other to achieve the correct sensing distance between the transmitter 22 and receiver 23.

FIG. 2 diagrammatically illustrates ear 25 having helix 27 and antihelix 29. The external canal opening 37, targus 35, concha 31 and lobe 33 are also illustrated. It is believed that the user of the BGD can be trained to insert BGD 12 over each test cycle at a substantially singular helix and antihelix position and capture an IR transmission at substantially the same position on antihelix 29. As indicated in the prior art, the positioning of the BGD on either the finger web or the antihelix over each repetitive glucose testing cycle is important. Also, the prior art indicates that the spacing between the IR transmitter and receiver should be maintained over each repetitive glucose testing cycle. For this reason, the correct positional location of the sensing channel on the finger web or the antihelix and the correct IR transmission distance is announced audibly and visually to the user during each glucose test.

The U-shaped sending channel 19 forms a mechanical stop near the inboard end of channel 19 which prohibits the further insertion of web 5 or helix 27. Stress relief channel 21 is too narrow to receive web 5 or helix 27.

Figure 3:
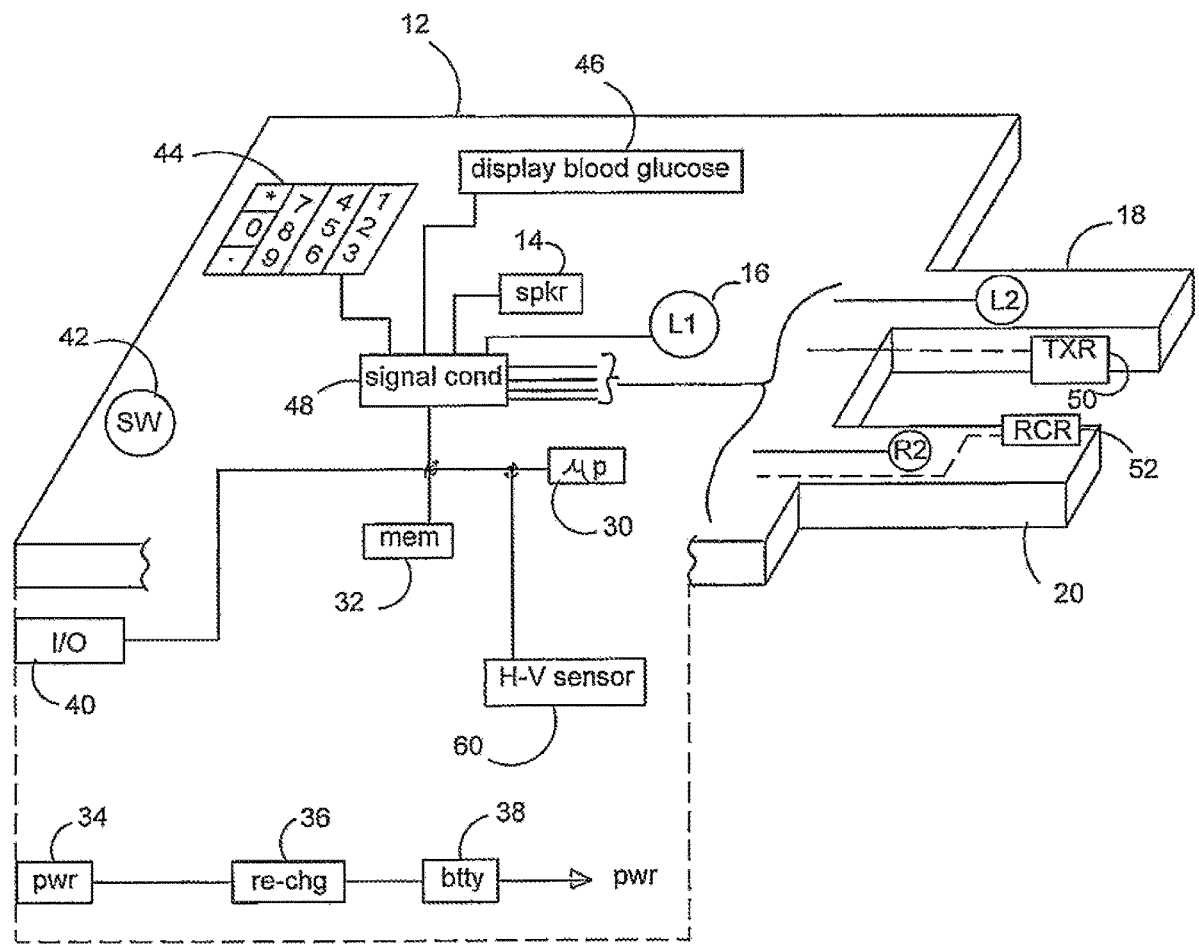
FIG. 3 diagrammatically illustrates, in block diagram form, the blood glucose detector and electrical components associated therewith.

FIG. 3 diagrammatically illustrates, in block diagram form, the major components of one embodiment of the blood glucose detector. Housing 12 includes on/off switch 42 and a display pad 44. Preferably, display pad 44 has indicia 1-9, 0, an asterix and a period. IR transmitter 50 is located at one inboard surface of leg 18 and IR receiver 52 is located at an inboard position on leg 20. Additionally, a positional light transmitter (txr) and receiver (rcr) sub-system is used in one embodiment. The positional light transmitter L2 and positional light receiver R2 are located inboard and closer to the confluence of leg 18 and leg 20. The positional sensors are substantially adjacent the forward end of housing 12 and the confluence of legs 18,20. The inboard end of sensing channel 19 is better shown in FIG. 1 (excluding stress relief channel 21) and inboard end region 60 in FIG. 4A.

The BGD is controlled by a processor, preferably microprocessor 30, operating in conjunction with memory 32 (mem). Power is supplied to the system via a power (pwr) port 34, a recharging (re-chg) subsystem 36 and a battery (btty) 38. Preferably, the BGD is a digital device with which accepts digital information and outputs digital information via input/output I/O port 40. Processor 30, memory 32 and port 40 are connected to each other via a common bus. A signal conditioner 48 converts any signals generated by the microprocessor into signals compatible to drive keypad 44 and BG level display monitor 46 (the user-understood displayed blood glucose number to be presented on display 46) and to drive speaker (spkr) 14 and positional indicator light 16 (L1). Further, signal conditioner 48 is coupled to IR transmitter 50, IR receiver 52 as well as positional detector light subsystem L2 and R2.

In connection with the antihelix BGD, the device includes a horizontal—vertical sensor subsystem 60. A recent breakthrough in Hall-effect sensing has enabled the creation of omnidirectional magnetic sensor ICs. Advances in IC design and fabrication now support the construction of vertical Hall sensors. The vertical and planar sensors are based on the same physical phenomena but different construction methods: (1) Planar: Laid out across the width and length of the chip; will only sense Z dimension regardless of orientation (2) Vertical: Constructed from top to bottom along the depth of the chip; can be oriented to sense X, Y, or other directions. See https://www.allegromicro.com/en/Insights-and-Innovations/Technical-Documents/Hall-Effect-Sensor-IC-Publications/Vertical-Hall-Tamper-Detection.

Operationally, the following initialization process and blood glucose detection process is followed.

Initialization Process

| Step | Description |
|---|---|
| 1. | Start up BGD |
| 2. | User input initialization start code (e.g. "000") |
| 3. | L1 blinks |
| 4a. | User places U-channel of F-web or antihelix |
| 4b. | User compresses Inboard and Outboard leg together (option) |
| 5. | L2-R2 and sensory sys registers "good placement" |
| 6. | L1 full ON |
| 7. | Audio Spkr Announce (ON) |
| 8. | 1550 nm sensory sys active |
| 9. | Sys records detected BG level (Txr-Rcr) |
| 10. | L1 full ON-long, then OFF-short |
| 11. | Audio Spkr ON-long, then OFF-short the ON-long (ON) |
| 12. | User withdraws BGD from F-web or antihelix |
| 13. | Within 2 minutes (t-out), User inputs blood glucose (BG) data from conventional machine via keypad (baseline BG data input) |
| 14. | User input initialization end code |

BG Detection Process

| Step | Description |
|---|---|
| 2.1 | Start up BGD |
| 2.2 | Start up BGD |
| 2.3 | L1 blinks |
| 2.4a | User Places U-channel on F-web or antihelix |
| 2.4b | User compresses Inboard and Outboard leg together (option) |
| 2.5 | L2-R2 sensory sys registers "good" |
| 2.6 | L1 full ON |
| 2.7 | Audio Spkr Single Beep (ON) |
| 2.8 | Sys record detected BG level (Txr-Rcr) |
| 2.9 | L2 full On-long, then OFF-short then ON-long |
| 2.10 | Audio Spkr On-long, then OFF-short then ON-long (ON) |
| 2.11 | User withdraws BGD from F-web or antihelix |
| 2.12 | Sys compares currently sensed or detected BG data with baseline BG data |
| 2.13 | Sys displays BG data on display screen for t-display |
| 2.14 | Sys. Stores: L2-R2(option sensor level at good placement; current BG daa; for antihelix: the H position |

To summarize the initialization process, the user must instruct or command the BGD to enter an initialization program stored in memory 32 and executed by processor 30. Earlier, the user has obtained his or her BG baseline data from a conventional device. The user then determines whether to place the BGD on his or her finger web or antihelix. The user inserts the web into sensory channel 19 or the antihelix into channel 19. Dependent upon whether the system utilizes a fixed leg system 18, 20 which does not have semi rigid but flexible legs, or if the user has a BGD system with rigid but semi-flexible legs (see stress relief channel 21 in FIG. 1 and flex systems in FIGS. 4A, 4B and 4C), the user then compresses legs 18, 20 together. The fixed leg system needs no leg compression. When positional light sensors L2 and R2 at the inboard end of sensory channel 19 indicate a good placement based upon the insertion position of web 5 or antihelix 29 in channel 19, the user's positional indicator light L1 (light 16) goes ON and, in a preferred embodiment, speaker 14 produces a beep sound or an annunciated phrase "good position".

Thereafter, the IR sensory system txr 50, rcr 52 is automatically activated thereby generating a detected blood glucose (BG) signal. Processor 30, in conjunction with memory 32, logs that detected BG blood glucose signal into memory (the log includes date and time data). In the sensing operation discussed below, the BG signal is then compared against an earlier stored baseline blood glucose data input by the user in step 13. For ease of use during the initialization phase, the user withdraws the BGD from the web or antihelix. The user then inputs the earlier obtained blood glucose data, obtained by conventional devices, into the BGD via keypad 44. The user then enters an OFF initialization position command.

In this manner, the user has input baseline blood glucose data which he or she has obtained from a conventional device prior to the initialization sub-program and the BGD has obtained a corresponding detected blood glucose signal based upon the 1550 IR signal transmitted through the web or the antihelix. The processor either converts the input baseline BG data to a "baseline detected BG signal" at the initialization phase or the processor converts the then initially detected BG signal into a "corresponding baseline BG data." The former may be preferable (using the converted baseline detected BG data). In any event, the processor and memory uses a BG baseline and compares that baseline to the then obtained BG detected signal, that is the repetitively obtained BG IR data.

During initialization, the user may input the BG baseline data into the BGD via keypad 44. Alternatively, the healthcare professional may initialize the BGD and upload the BG baseline data into the BGD memory via I/O port 40 for the user. Prior art references calibrate non-invasive blood glucose (BG) measuring systems by correlating invasively and non-invasively acquired BG data. In the present invention, the initialization process creates the BG baseline data set with invasive BG data correlated to non-invasive BG data obtained from the BGD.

It should be noted that the steps for the initialization process and the steps for the BG detection process may be reorganized to provide for a more efficient operation. Also, it should be noted that processor 30 and memory 32 and potentially signal conditioner 48 may be combined in a single integrated circuit(IC). Programmable IC circuits may also be utilized. For example, there are ICs with built-in comparator circuits.

In connection with the antihelix BGD, the horizontal—vertical sensor 60 is utilized to detect the repetitive test-to-test angle insertion over helix 27 and onto antihelix 29. The angle of attack, either V1 or H1 or something in between is stored into memory by data from the H-V sensor subsystem 60, initially obtained during the initialization process. To assure substantially the same test-to-test angular positions on the antihelix, the processor stores in memory the angle of attack V1, H1 or angle X1 into memory during the initialization process. This initial angle of attack data (V1, H1 or other angle X1) is compared against then acquired angle of attack data from the H-V sensor and, in a match or a substantial match (maybe+/−10 degrees), the position indicator light illuminates and the speaker announces a "good position" audio indicator.

As an alternative to the lighted positional sensor in FIGS. 1 and 3, any type of positional sensors may be used such as electric tactile sensors, EMF sensors, temperature sensors, etc. The key element is to detect the proper, repetitive insertion of the web or antihelix into channel 19.

Figure 4A:
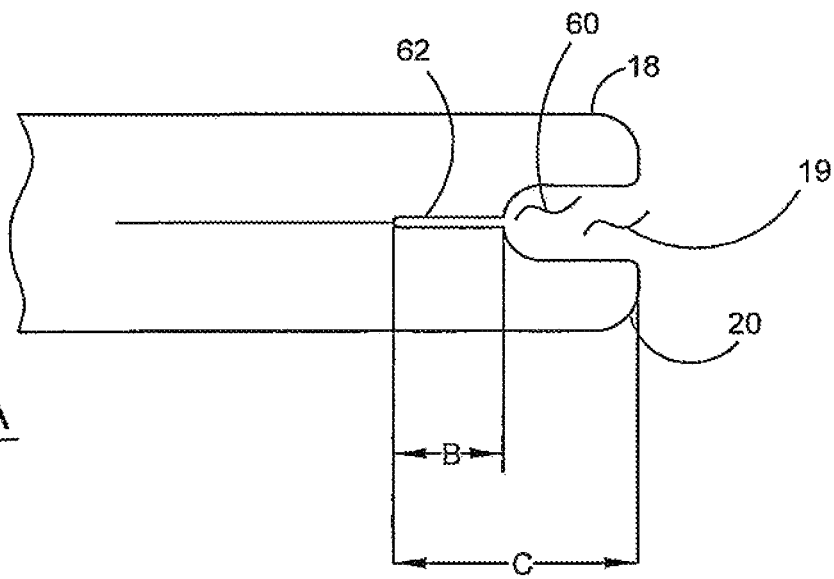
FIGS. 4A, 4B and 4C diagrammatically illustrate other mechanical constructions for the blood glucose detector, namely the flexible legs.

FIG. 4A diagrammatically illustrates that stress relief channel 62 has a longitudinal distance B which is significantly smaller than the combined longitudinal leg distance C. Stress relief channel 62 is located adjacent inboard end 60 of channel 19, that is, near the confluence of legs 18, 20. End 60 forms a mechanical stop for channel 19.

Figure 4B:
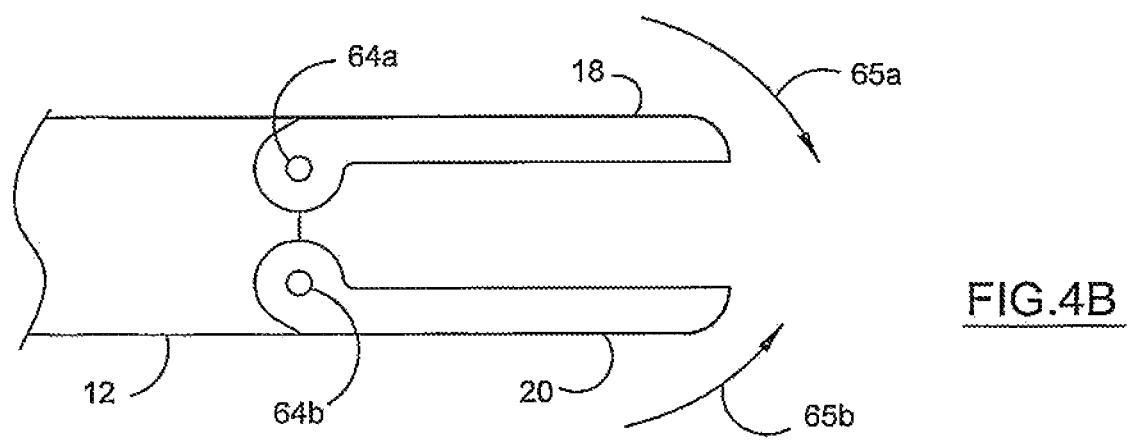

FIG. 4B diagrammatically shows that legs 18, 20 are pivotally mounted to housing 12 at pivot points 64a, 60b. In this manner, leg 18 rotates in direction 65a and leg 20 rotates in direction 65b. Also, legs 18, 20 have counter bias elements (springs or resilient mechanical components) which force legs 18, 20 apart after the compression step 65a, 65b.

Figure 4C:
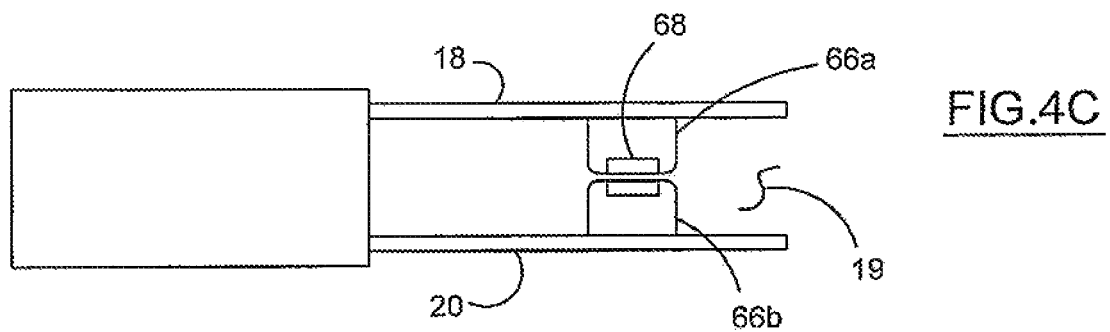

FIG. 4C diagrammatically shows that leg 18 has an inwardly protruding detent 66a on the leg's inboard surface. Detent 66a has either a positional light sensor 68 operable with a positional light sensor detector (not numbered in FIG. 4C). Alternatively, inwardly protruding detents 66a, 66b may have a positional sensor subsystem that senses the distance between the distal inboard services of the detents in order to determine the proper leg-to-leg spacing for sensory channel 19. As a leg-to-leg space positional detection subsystem, an induction or magnetic spatial detection subsystem may be used. Using a Hall element with analog output makes it possible to detect the position of an object by resolving power in the order of a few micrometers for a stroke of 1 mm. See https://www.akm.com/akm/en/product/add/magnetic_sensors/0002/.

Figure 5:
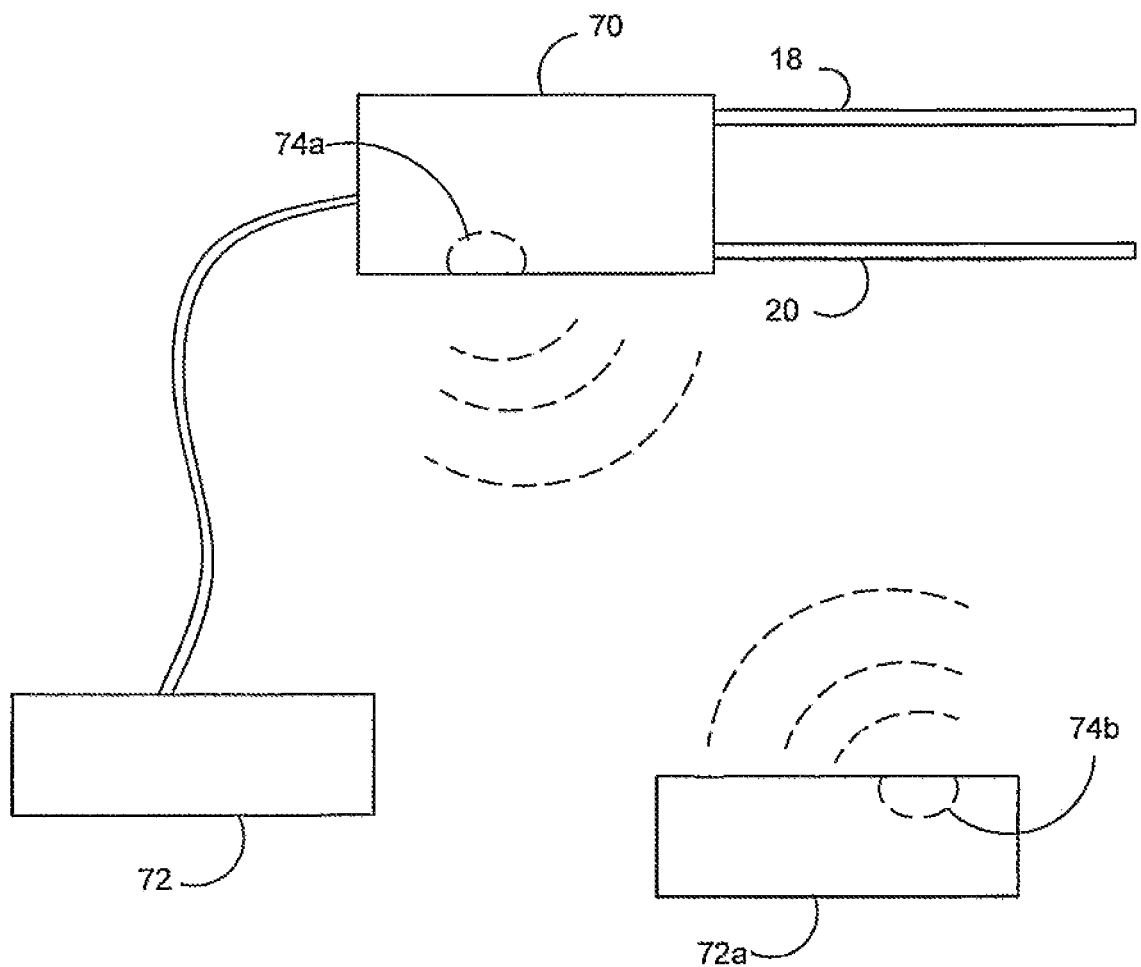
FIG. 5 diagrammatically illustrates a blood glucose detector which is partly configured as a two component system, with one component to be inserted on a finger web or anti-helix and a second component which is a remote control unit either in a wired configuration (see wired control unit 72) and a wireless configuration (see RF signals from and to unit 72) utilizing Bluetooth or other wireless connection with the blood glucose detector component 70, used in conjunction with a finger web or an antihelix.

FIG. 5 diagrammatically shows a two piece BGD. Housing 70 includes primarily the mechanical and sensory components of the blood glucose detector with opposing legs 18, 20. However, the two piece BGD has a remote display and controller component 72 which is coupled by a wire to the web detector or antihelix detector component 70. Alternatively, remote control unit 72a may be linked via a wireless network using transmitter—receiver 74a, 74b which cooperates and provides a data transmission path via transceiver 74a in mechanical BGD component 70. The remote unit 72a may be a cell phone with an operable App.

In other embodiments, the keypad may be replaced by a touch screen display which, during initialization, shows a keypad to enable the user to input baseline BG data into the BGD. In this manner BG display panel 46 is replaced by the touch screen which also acts as a BG level display monitor. BG display 46 receives a BG displayable signal produced by the processor and the memory. Also, the processor converts the then detected BG signal into a corresponding BG displayable signal (a data conversion routine) such that the user can compare the then detected BG signal to the doctor recommended BG level.

During the detection cycle, the BGD may announce via the speaker and/or the indicator light that the BGD has completed its processing and has displayed the BG level on display 46 to the user.

Typically, the inboard sensory channel end 60 (FIG. 4A) acts as a mechanical stop for the web or helix. However, the outboard surfaces of detents 66a, 66b in FIG. 4C may also act as the mechanical stop for the web or helix.

The present invention could be produced in hardware or software, or in a combination of hardware and software, and these implementations would be known to one of ordinary skill in the art. The system, or method, according to the inventive principles as disclosed in connection with the preferred embodiments, may be produced on a single computer IC chip having separate elements or means for performing the individual functions or steps described or claimed or one or more elements or means combining the performance of any of the functions or steps disclosed or claimed, or may be separate IC components interconnected by any suitable means.

According to the inventive principles as disclosed in connection with the preferred embodiments, the invention and the inventive principles are not limited to any particular kind of computer chip system but may be used with any general purpose processor, as would be known to a person of ordinary skill in the art, arranged to perform the functions described and the method steps described herein. The operations of such a processor and memory, as described above, may be according to a computer program contained on a medium for use in the operation or control of the processor, as would be known to person of ordinary skill in the art. The computer medium which may be used to hold or contain the computer program product, may be a fixture of the computer such as an embedded memory or may be on a transportable medium such as a disk, as would be known to one of ordinary skill in the art.

The invention is not limited to any particular computer program or logic or language, or instruction but may be practiced with any such suitable program, logic or language, or instructions as would be known to one of ordinary skill in the art. Without limiting the principles of the disclosed invention any such computing system can include, inter alia, at least a computer readable medium allowing a processor to read data, instructions, messages or message packets, and other computer readable information from the computer readable medium. The computer readable medium may include non-volatile memory, such as ROM, flash memory, or other optical memory storage devices, and other permanent storage. Additionally, a computer readable medium may include, for example, volatile storage such as RAM, buffers, cache memory, and network circuits.

Furthermore, the computer readable medium may include computer readable information in a transitory state medium such as a network link and/or a network interface, including a wired network or a wireless network, that allow a computer to read such computer readable information.

The claims appended hereto are meant to cover modifications and changes within the scope and spirit of the present invention.

What is claimed is:

1. A blood glucose detector adapted to be placed on a user's finger web or an ear's antihelix and used in conjunction with earlier obtained baseline blood glucose data set comprising:
a housing having, at one end, opposing legs extending from said housing forming a substantially U-shaped sensing channel adapted to receive said finger web or ear antihelix during a detection mode, said U-shaped channel forming a mechanical stop which limits further insertion of said finger web or ear antihelix during said detection mode;
a positional light sensor substantially adjacent said stop coupled to an audible or lighted indicator system adapted to indicate a detection position to said user;
a blood glucose sensor on one or both of said opposing legs at an outboard position relative to said positional light sensor, said blood glucose sensor having a transmitter transmitting light into said finger web or ear antihelix within a 1550 nm bandwidth range wherein said 1550 nm bandwidth range is 1085 nm to 2015 nm, said blood glucose sensor having a signal generator generating a detected blood glucose signal;
a processor coupled to a memory, said processor, coupled to said blood glucose sensor, said memory storing therein said baseline blood glucose data set, said processor correlating said detected blood glucose signal with said baseline blood glucose data set and generating a displayable blood glucose level during said detection mode for comparison with a healthcare recommended blood glucose level; and
a display module for displaying said displayable blood glucose level during said detection mode, said display module coupled to said processor.

2. The blood glucose detector as claimed in claim 1 wherein said processor includes a detection completion indicator system adapted to indicate a completed detection cycle to said user substantially upon generation of said displayable blood glucose level.

3. The blood glucose detector as claimed in claim 1 wherein said processor logs and stores into said memory said baseline blood glucose data set, said detected blood glucose signal, and said displayable blood glucose level as logged data.

4. The blood glucose detector as claimed in claim 1 including a data output port coupled to said processor and said memory to output logged data.

5. The blood glucose detector as claimed in claim 1 wherein said opposing legs extend outboard from said housing and respective inboard surfaces of said opposing legs form said stop.

6. The blood glucose detector as claimed in claim 1 wherein said opposing legs extend outboard from said housing and wherein at least one leg is semi-rigid and flexible such that during said detection mode, said at least one leg is adapted to flex towards the other leg by said user.

7. The blood glucose detector as claimed in claim 6 wherein said at least one leg has a flexible element, wherein said flexible element is a stress relief joint, a stress relief channel, a hinge coupling said at least one leg to said housing or a biased pivot joint at said at least one leg and said housing.

8. The blood glucose detector as claimed in claim 6 wherein said positional light sensor is spaced away from but substantially adjacent to said stop, said positional light sensor being activated during a flexation of said at least one leg towards said other leg.

9. The blood glucose detector as claimed in claim 6 wherein said opposing legs include a first leg and a second leg, the detector including an inwardly protruding detent extending into said U-shaped channel from said first leg towards said second leg, said detent having a distal surface region spaced from said first leg and an outboard detent surface, said positional light sensor located on said distal surface region, and said outboard detent surface acting as said stop.

10. A blood glucose detector adapted to be placed on a user's finger web or an ear's antihelix and used in conjunction with earlier obtained baseline blood glucose data set comprising:
a housing having, at one end, opposing legs extending from said housing forming a substantially U-shaped sensing channel adapted to receive said finger web or ear antihelix during a detection mode, said U-shaped channel forming a mechanical stop which limits further insertion of said finger web or ear antihelix during said detection mode;
said opposing legs including a first leg and a second leg, an inwardly protruding detent extending into said U-shaped channel from said first leg towards said second leg, said detent having a distal surface region spaced from said first leg and an outboard detent surface, said outboard detent surface acting as a mechanical stop;
a positional sensor on said distal surface region coupled to an audible or lighted indicator system adapted to indicate a detection position to said user;

a blood glucose sensor on one or both of said opposing legs at an outboard position relative to said positional light sensor, said blood glucose sensor having a transmitter transmitting light into said finger web or ear antihelix within a 1550 nm bandwidth range wherein said 1550 nm bandwidth range is 2015 nm to 1085 nm, said blood glucose sensor having a signal generator generating a detected blood glucose signal;

a processor coupled to a memory, said processor, coupled to said blood glucose sensor, said memory storing therein said baseline blood glucose data set, said processor correlating said detected blood glucose signal with said baseline blood glucose data set and generating a displayable blood glucose level during said detection mode for comparison with a healthcare recommended blood glucose level; and a display module for displaying said displayable blood glucose level during said detection mode, said display module coupled to said processor.

11. The blood glucose detector as claimed in claim 10 wherein said positional sensor includes one positional sensing element on said distal surface region and a second positional sensing element on said second leg, opposite said one positional sensing element.

12. A blood glucose detector adapted to be placed on a user's finger web or an ear's antihelix and used in conjunction with earlier obtained baseline blood glucose data set comprising:

a housing having, at one end, opposing legs extending from said housing forming a substantially U-shaped sensing channel adapted to receive said finger web or ear antihelix during a detection mode, said U-shaped channel forming a mechanical stop which limits further insertion of said finger web or ear antihelix during a detection mode;

said housing including a processor coupled to a memory, a display coupled to said processor and memory, said memory storing said baseline blood glucose data set, a user actuatable input coupled to said processor and said memory, and an audio annunciation module coupled to said processor and said memory;

a positional sensor, substantially adjacent said stop, coupled to said processor and generating positional signals to said processor, said processor activating audible and lighted indicator systems via said audio module and said display to indicate a detection position for said U-shaped channel over said finger web or said antihelix;

a blood glucose sensor on one or both of said opposing legs at an outboard position relative to said positional sensor, said blood glucose sensor having a transmitter transmitting light into said finger web or ear antihelix within a 1550 nm bandwidth range wherein said 1550 nm bandwidth range is 1085 nm to 2015 nm, said blood glucose sensor having a signal generator generating a detected blood glucose signal;

said processor coupled to said blood glucose sensor and receiving said detected blood glucose signal, said processor correlating said detected blood glucose signal with said baseline blood glucose data set, said processor generating a displayable blood glucose level data during said detection mode, said displayable blood glucose level data enabling user comparison with a healthcare recommended blood glucose level, said processor applying said displayable blood glucose level data to said display; and said processor having a detection completion indicator module adapted to indicate, either audibly or visually, a completed detection cycle to said user substantially upon generation of said displayable blood glucose level data.

13. The blood glucose detector as claimed in claim 12 wherein said processor having means for storing logged data in said memory wherein the logged data includes said baseline blood glucose data, said detected blood glucose signal and said displayable blood glucose level data.

14. The blood glucose detector as claimed in claim 12 including an input port coupled to said processor, said processor having an initialization module accepting said baseline blood glucose data set via said input port and storing the same in said memory.

15. The blood glucose detector as claimed in claim 12 including an input/output port coupled to said processor, said processor having an initialization module which either (a) accepts said baseline blood glucose data set via said input/output port and stores the same in said memory, or (b) is adapted to accept said baseline blood glucose data set via said keypad from said user.

16. The blood glucose detector as claimed in claim 12 wherein said at least one leg has a flexible element, wherein said flexible element is a stress relief joint, a stress relief channel, a hinge coupling said at least one leg to said housing or a biased pivot joint at said at least one leg and said housing.

17. The blood glucose detector as claimed in claim 12 wherein said positional sensor is spaced away from but substantially adjacent to said stop, said positional sensor being activated during a flexation of said at least one leg towards said other leg.

18. The blood glucose detector as claimed in claim 12 wherein said opposing legs include a first leg and a second leg, the detector including an inwardly protruding detent extending into said U-shaped channel from said first leg towards said second leg, said detent having a distal surface region spaced from said first leg and an outboard detent surface, said positional sensor located on said distal surface region, and said outboard detent surface acting as said stop.

19. A method of detecting blood glucose via infared (IR) light, said IR light adapted to be transmitted through a user's finger web or an ear's antihelix, the method comprising:

obtaining a baseline blood glucose data set unique to said user;

storing said baseline blood glucose data set in a memory;

providing a substantially U-shaped sensing channel adapted to receive said finger web or ear antihelix during a detection mode;

limiting insertion of said finger web or ear antihelix into said U-shaped sensing channel during a detection mode;

audibly and visually indicating a sensing position when said finger web or ear antihelix is at or adjacent a mechanical stop;

while at said sensing position, transmitting IR light into said finger web or ear antihelix within a 1550 nm bandwidth range wherein said 1550 nm bandwidth range is 1085 nm to 2015 nm and generating a detected blood glucose signal;

correlating said detected blood glucose signal with said baseline blood glucose data set to obtain a blood glucose value enabling comparison with a healthcare recommended blood glucose level;

displaying a blood glucose value during said detection mode;

indicating, either audibly or visually, a detection completion when said blood glucose value is displayed.

20. The method of detecting blood glucose as claimed in claim 19 including logging and storing into said memory: said baseline blood glucose data, said detected blood glucose signal and said blood glucose value as logged data.

21. The method of detecting blood glucose as claimed in claim 19 and obtaining said baseline blood glucose data set via an input port and storing the same in said memory.

22. The method of detecting blood glucose as claimed in claim 19 and obtaining said baseline blood glucose data set via a user actuatable input and storing the same in said memory.

* * * * *